(12) United States Patent
Chan et al.

(10) Patent No.: US 8,080,582 B2
(45) Date of Patent: Dec. 20, 2011

(54) DERIVATIVES OF 8-EPIBLECHNIC ACID AND THEIR EFFECTS ON DOWN-REGULATION OF ENDOTHELIN (ETA) RECEPTOR MRNA

(75) Inventors: Hardy Chan, San Mateo, CA (US);
Chung Faye Chao, Taipei (TW);
Vallapa Soong, Yungkang (TW)

(73) Assignee: ScinoPharm Taiwan Ltd., Tainan (TW)

( * ) Notice: Subject to any disclaimer, the term of this patent is extended or adjusted under 35 U.S.C. 154(b) by 361 days.

(21) Appl. No.: 12/542,833

(22) Filed: Aug. 18, 2009

(65) Prior Publication Data
US 2010/0048618 A1  Feb. 25, 2010

Related U.S. Application Data

(60) Provisional application No. 61/189,420, filed on Aug. 19, 2008.

(51) Int. Cl.
*A61K 31/343* (2006.01)
*C07D 307/80* (2006.01)

(52) U.S. Cl. ........................ 514/469; 549/467

(58) Field of Classification Search ............... 514/469; 549/467
See application file for complete search history.

(56) References Cited

FOREIGN PATENT DOCUMENTS
WO    WO 2004/012651    2/2004

OTHER PUBLICATIONS

Zhou et al., Effect and mechanism of salvianolic acid B in attenuating elevated portal pressure in a rat model of portal hypertension induced by endothelin-1, Zhong Xi Yi Jie He Xue bao, 5(1), pp. 61-64, Jan. 2007, Abstract only.
Orry et al., Modeling and Docking the Endothelin G-Protein-Coupled Receptor, Biophysical Journal, vol. 79, pp. 3083-3094, Dec. 2000, p. 30830p. 3091.

*Primary Examiner* — Taofiq A Solola
(74) *Attorney, Agent, or Firm* — Kent H. Cheng; VLP Law Group LLP

(57) ABSTRACT

The present application discloses derivatives of 8-epiblechnic acid and use thereof in treating a disease related to endothelin receptor A or endothelin-1 (ET-1) over-expression, such as hypertension, cancer, atherosclerosis, and myocardial infarction.

15 Claims, 5 Drawing Sheets

DERIVATIVES OF 8-EPIBLECHNIC ACID AND THEIR EFFECTS ON DOWN-REGULATION OF ENDOTHELIN (ETA) RECEPTOR MRNA

RELATED APPLICATIONS

This application claims priority from U.S. Provisional Patent Application Ser. No. 61/189,420 which was filed on Aug. 19, 2008. The entire content of this application is herein incorporated as reference.

BACKGROUND OF THE INVENTION

1. Field of the Invention

The present application relates to derivatives of 8-epiblechnic acid and use thereof in treating a disease related to endothelin receptor A or endothelin-1 (ET-1) over-expression.

2. Description of the Related Art

Cancer arises in a multi-step process with complex formative causes. ET-1 participates in the formation and development of many types of tumors via endothelin receptor type A (ETAR) and endothelin receptor type B (ETBR), such as prostate cancer, ovarian cancer, renal cancer, lung cancer, colon cancer, melanoma, cervical cancer, bone cancer, breast cancer, Kaposi's sarcoma, and some central nervous system tumors.

ET-1 and its receptors (ETAR and ETBR) are over-expressed in breast carcinomas and appear to influence tumor growth and progression (*British Journal of Cancer* (2004) 91, 434-440).

Clinical tests have proven that endothelin receptor type A antagonist (Atrasentan, ABT-627) can treat prostate cancer. In summary, ET-1 plays an important role in the physiological mechanism of cancer, and can promote tumor growth via specific endothelin receptors. Because of this, endothelin receptor antagonists provide a novel and important means for treating cancers.

Lithospermic acid B (Salvianolic acid B, Sal-B) has been identified as an active component in an extract of *Salvia miltiorrhiza* radix that was shown to exhibit endothelium-dependent vasodilatation in the aorta and may be useful in the treatment of hypertension (see Kamata, et al., 1993, Gen. Pharmacol. 24, 977-981). Sal-B is a water-soluble phenolic acid extracted from *Salvia miltiorrhiza*; its anti-tumor efficacy has been disclosed in Chinese patent application No. CN1408353A.

It has been found that the blood of hypertension patients contains higher levels of ET-1 than that of normal persons, and it has been discovered that ET-1 has a major influence on the developments of cardiovascular diseases in humans, such as hypertension, atherosclerosis, and myocardial infarction (Schmitz-Spanke, 2000). Other researchers have found that, after treating rats with the ETAR antagonist BQ-123 in the animal model of induced-hypertension, the symptoms of hypertension and ventricular enlargement can be eased. (Yamazaki, 1996; Barton, 1998; Matsumura, 1999; Dao, 2001; Park, 2001).

There is still a need to develop the analogs of Sal-B as the drugs to sufficiently treat the diseases related to the over-expression of ET-1 or endothelin receptor via inhibiting the expressions of endothelin receptors. The diseases include tumor growth and metastasis, as well as cardiovascular diseases, e.g. hypertension, atherosclerosis, and myocardial infarction.

SUMMARY OF THE INVENTION

The present application provides a compound of formula (I) or a salt thereof

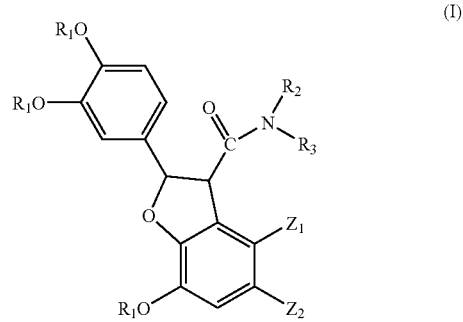

(I)

wherein
$R_1$ is $C_1$-$C_6$ alkyl, phenyl, benzyl, or a hydroxyl protecting group each of $Z_1$ and $Z_2$ is independently H or C=C—CO—$NR_2R_3$ optionally substituted with $C_1$-$C_6$ alkyl on the vinyl group with the proviso that one of $Z_1$ and $Z_2$ is H, and $Z_1$ and $Z_2$ are not H at the same time;
$R_2$ is H,
$R_3$ is

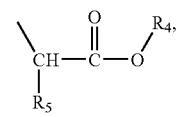

or $R_2$ and $R_3$ together form an optionally substituted 5-7 membered monocyclic ring or an optionally substituted 8-12 membered bicyclic ring;
$R_4$ is $C_1$-$C_6$ alkyl, allyl, phenyl, or benzyl; and
$R_5$ is $C_1$-$C_6$ alkyl, mercaptomethyl, 1-H-imidazol-4-ylmethyl, methylthioethyl, pyrrolidinyl, hydroxylmethyl, hydroxylethyl, or methylbenzyl unsubstituted or substituted with 1-3 hydroxyl, methoxy or ethoxy.

Preferably, $R_1$ is methyl.
Preferably, $Z_2$ is H, $Z_1$ is C=C—CO—$NR_2R_3$ optionally substituted with $C_1$-$C_3$ alkyl on the vinyl group.
Preferably, $R_2$ is H, $R_3$ is

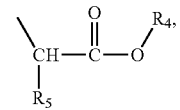

$R_4$ is methyl, and $R_5$ is isopropyl or methylbenzyl substituted with 0-3 hydroxyl, methoxy or ethoxy.
Preferably, $R_5$ is methylbenzyl substituted with 2 methoxy.
Preferably and alternatively, $R_5$ is unsubstituted methylbenzyl.
Preferably and alternatively, $R_5$ is isopropyl.
Preferably and alternatively, $R_2$ and $R_3$ together form an optionally substituted 8-12 membered bicyclic ring.

The hydroxyl protecting group can be any suitable group that can preventing an hydroxyl group connecting to a phenyl group from reacting with other compound. Such hydroxyl protecting group is also called phenol protecting group.

The compounds of the present invention may be used as an active ingredient for treating a disease related to endothelin receptor A or endothelin-1 over-expression by administering to a patient in need thereof an effective amount of compound of formula (I). The patient may be an animal, preferably a human. The disease may be hypertension, cancer, atherosclerosis, or myocardial infarction.

The compounds in accordance with the present invention can be formulated into a pharmaceutical composition together with a pharmaceutically acceptable carrier, e.g., bulking agent, binder, filler, wetting agent, disintegrating agent, surface active agent, and lubricant. Various types of administration unit forms can be selected depending on the therapeutic purposes, and the examples of pharmaceutical compositions are tablets, pills, powders, liquids, suspensions, emulsions, granules, capsules, suppositories, injection preparations (solutions and suspensions) and the like.

The amount of the compound of formula (I) or salt thereof to be contained in a pharmaceutical composition is not specifically restricted and can suitably selected from a wide range, for example, from 0.01 to 80% based on weight of the whole composition.

Administration methods of a pharmaceutical composition of the present invention are not specifically restricted, and can be administered in various forms of preparations depending on the age of the patient, distinction of sex, other conditions, as well as conditions of the symptoms. For example, tablets, pills, solutions, suspensions, emulsions, granules and capsules are orally administered; and injection preparations are administered singly or mixed with injection transfusions such as glucose solutions and amino acid solutions intravenously; and if necessary, the injection preparations are administered singly intramuscularly, intracutaneously, subcutaneously or intraperitoneally. Suppositories are administered into the rectum.

The dosage of a pharmaceutical composition according to the present invention are suitably selected according to the method of use, the age of the patient, distinction of sex, other conditions, as well as conditions of the symptoms, usually about 0.05 to 50 mg/kg of the body weight/day of the compound of general formula (I) as the active ingredient may be administered.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
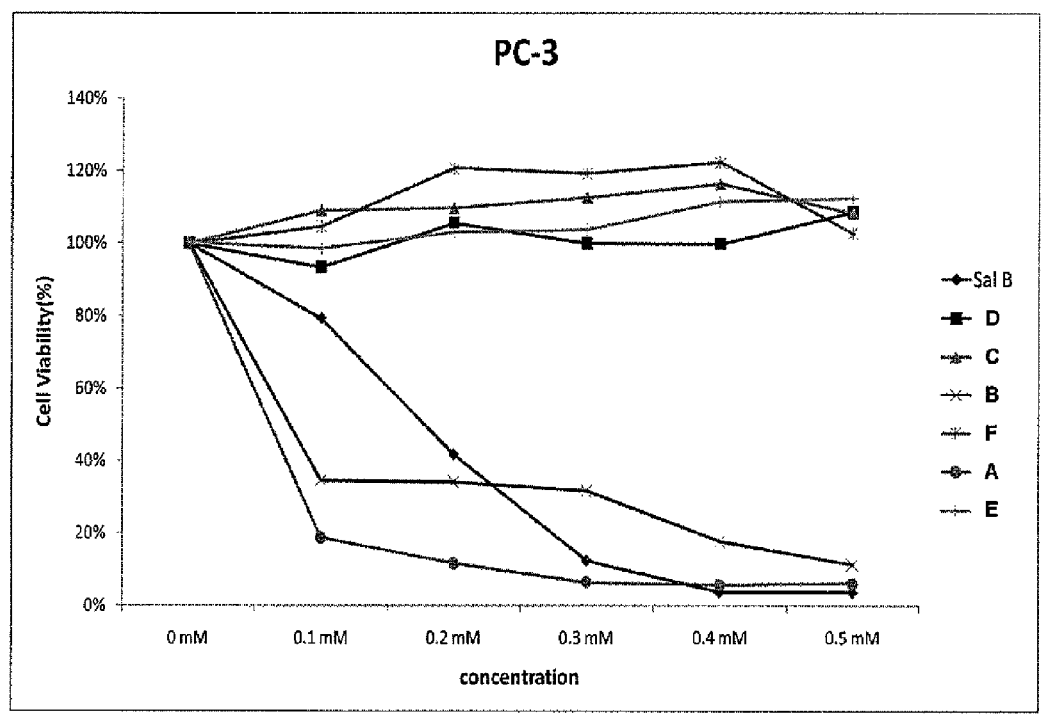
FIG. 1 illustrates the effects of Sal-B and Compounds A-F on the viability of cancer cells.

The following is presented to further illustrate, but not to limit, the present invention.

I. Preferred Compounds in Accordance with the Present Invention and Preparation Thereof The magnesium lithospermate B (Lithospermic acid B, Salvianolic acid B, Sal-B) was isolated from plant *Salvia miltiorrhiza* (Dan-Shen in Chinese).

The chemical structure of magnesium lithospermic acid B of formula II is shown below.

Formula II

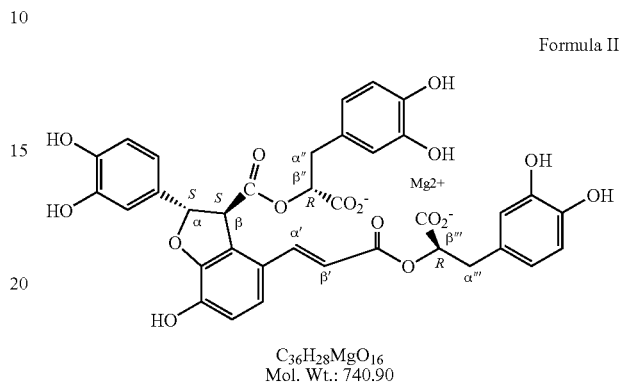

$C_{36}H_{28}MgO_{16}$
Mol. Wt.: 740.90

Compounds A to F in accordance with embodiment of the present invention are developed based on lithospermate B core structure. The structures of Compounds A-F and are shown below.

Compound A

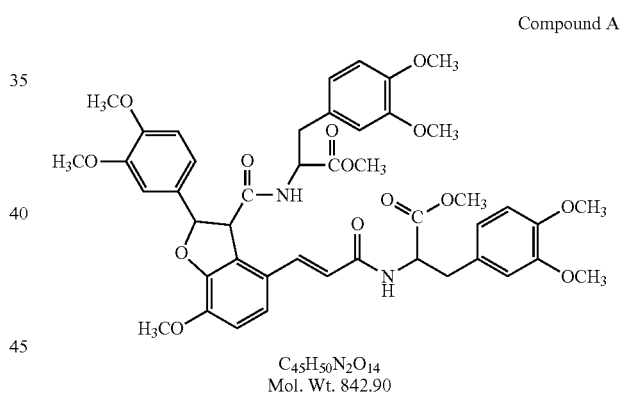

$C_{45}H_{50}N_2O_{14}$
Mol. Wt. 842.90

Compound B

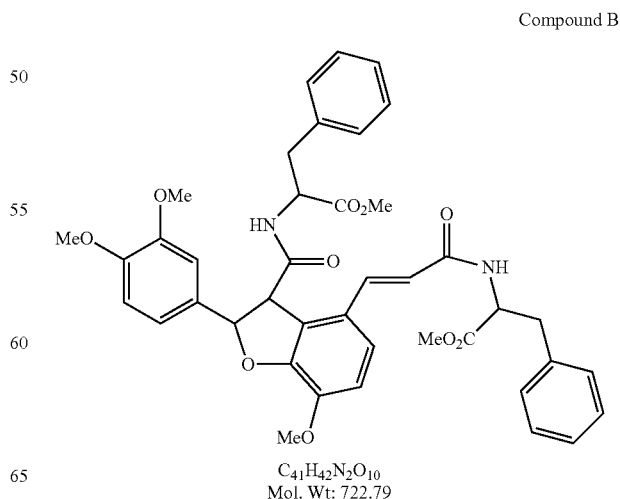

$C_{41}H_{42}N_2O_{10}$
Mol. Wt: 722.79

Compound C

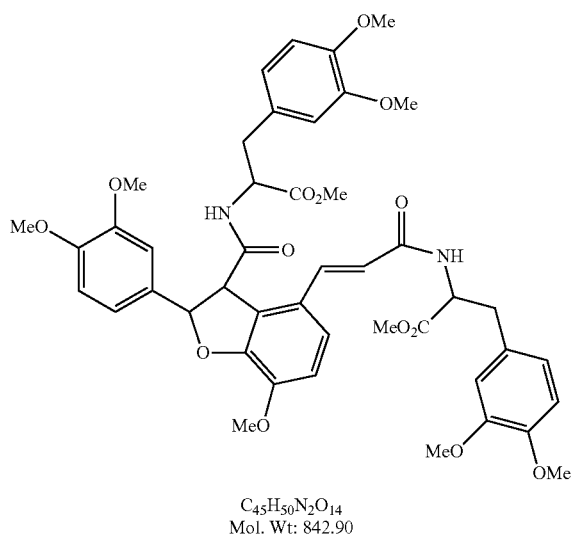

C₄₅H₅₀N₂O₁₄
Mol. Wt: 842.90

Compound D

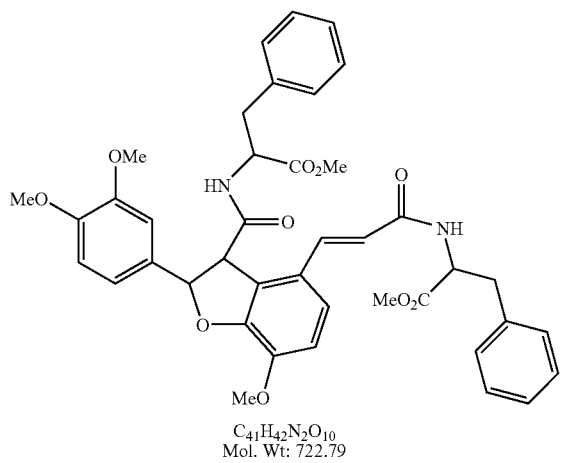

C₄₁H₄₂N₂O₁₀
Mol. Wt: 722.79

Compound E

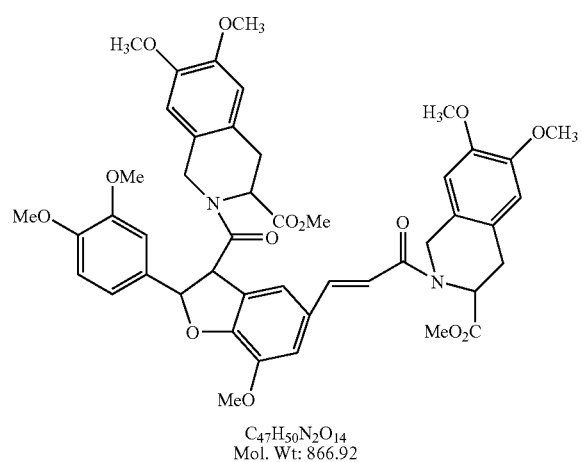

C₄₇H₅₀N₂O₁₄
Mol. Wt: 866.92

Compound F

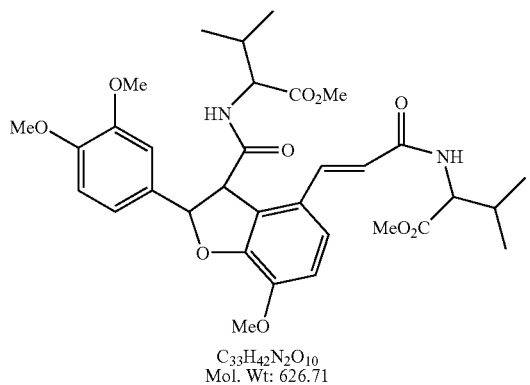

C₃₃H₄₂N₂O₁₀
Mol. Wt: 626.71

Process of making Compounds A-F in accordance with embodiments of the present invention is described below.

EXAMPLE 1

Example 1 illustrates process of making common intermediate IM1 for making Compounds A and B.

Extraction of Magnesium Lithospermate B

Dried powder of *Salvia miltiorrhiza* (4 kg) and water (12 kg) are charged to a suitable reactor. The mixture is soaked at room temperature (about 22-25° C.) for 18 hr. After filtration, the solid is washed with water (5 kg). The filtrate and washing solutions are combined and subjected to contact with sufficient amount of SP-850 resin to absorb the product. The SP-850 resin with absorbent is washed with water (16 kg) and eluted with MeOH (6.9 kg). The MeOH solution is distillated to its volume with about 500 mL left. The concentrated solution is chromatographed on a column with Sephadex LH-20. The column is eluted with water to provide the aqueous solution of magnesium lithospermate B. The water is removed by lyophilization to give dry magnesium lithospermate B product with 97% purity.

Conversion of Magnesium Lithospermate B Via Epiblechnic Acid (EBA) to Trimethyl Epiblechnic Acid (IM1)

Scheme 1:

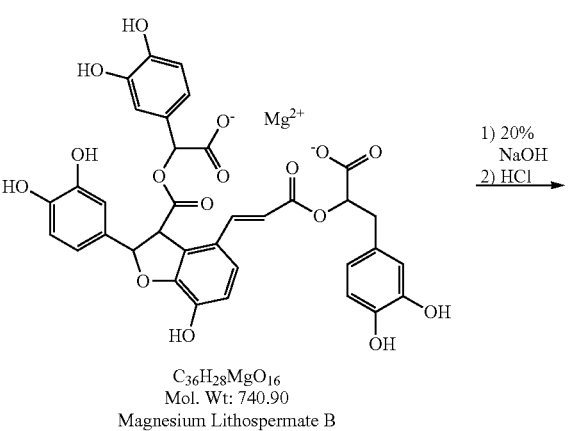

C₃₆H₂₈MgO₁₆
Mol. Wt: 740.90
Magnesium Lithospermate B

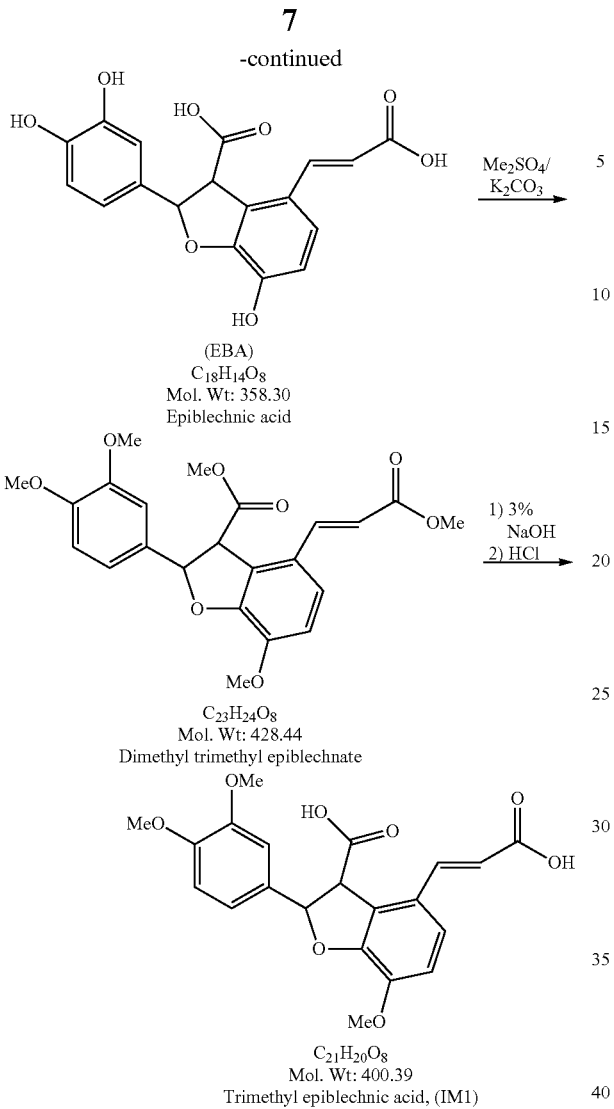

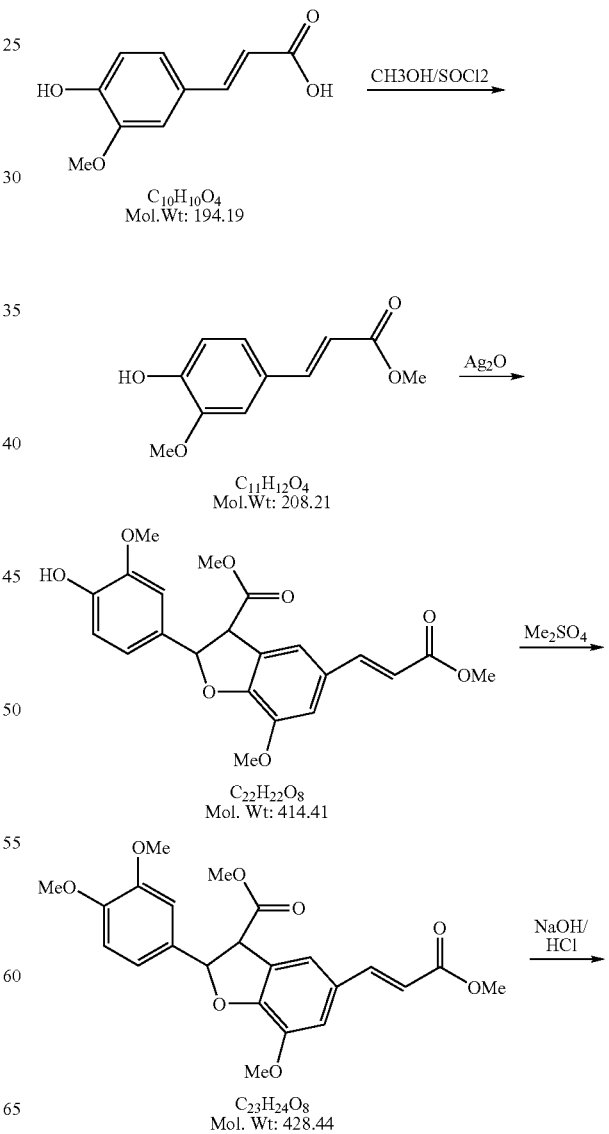

the mixture was distillated to remove acetone, adjusted to pH=3 with 1% HCl and added with ethyl acetate (30 mL) for extraction. The organic layer was separated and washed with brine (20 mL). The organic layer was distilled to give yellow oil (0.2 g). The yellow oil was purified by preparative thin layer chromatography to give 2 mg yellow solid trimethyl epiblechnic acid (IM1).

MS (TOF): 423(M+Na)$^+$, 823(2M+Na)$^+$

EXAMPLE 2

Example 2 illustrates process of making common intermediate IM2 for making compounds C to F Conversion of 3-methoxy-4-hydroxy cinnamic acid to IM2

Scheme 2:

0.5 g of magnesium lithospermate B (made in accordance with the process described above), 0.54 g of NaOH and 5 mL of H$_2$O were mixed and stirred at room temperature (~23° C.) for overnight. After reaction completed, the mixture was adjusted to pH=1 with 5% HCl and extracted with 50 mL of ethyl acetate. Ethyl acetate solution was added with magnesium sulfate and stirred for 1 hr. The mixture solution was filtered to remove the solid. The filtrate was concentrated to give crude epiblechnic acid. This crude was purified by chromatography on silica gel column with a 10:1 V/V mixture of butanol and acetic acid as eluent. After solvent distilled, 210 mg of epiblechnic acid (EBA) was produced. Its structure was confirmed by proton magnetic resonance spectroscopy.

1H-NMR(DMSO-d$_6$)δ: 12.00-13.00(2H, —COOH), 8.93 (1H, C4'-OH), 8.89(2H, C3,4-OH), 7.57(1H, d, J=16 Hz, H-7'), 7.18(1H, d, J=8 Hz, H-6'), 6.78(1H, d, J=8.8 Hz, H-5'), 6.71(1H, d, J=2.4 Hz, H-2), 6.70(1H, d, J=7.6 Hz, H-5), 6.66-6.20(1H, dd, J=2.0; 8.0 Hz, H-6), 6.23(1H, d, J=16 Hz, H-8'), 5.78(1H, d, J=4.4 Hz, H-7), 4.27(1H, d, J=4.4 Hz, H-8)

Dimethyl trimethyl epiblechnate (140 mg) and acetone (5 mL) were stirred for dissolution. K$_2$CO$_3$ (1.5 g) and Me$_2$SO$_4$ (1.5 mL) were added into the mixture and the solution was heated to reflux. Then, the solution mixture was stirred for 4 hr, cooled, added 3 mL of water, and stirred for 30 min. 3% NaOH was added to the solution. After reaction completed, -continued

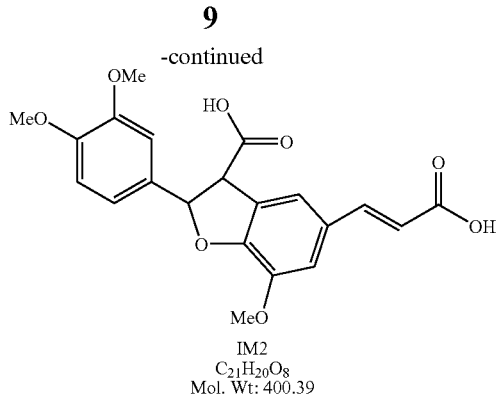

IM2
C₂₁H₂₀O₈
Mol. Wt: 400.39

5 g of 3-methoxy-4-hydroxy cinnamic acid and 50 mL of methanol (MeOH) were mixed and stirred for dissolution. SOCl₂ was added to the solution mixture and stirred at 20-70° C. for 1 hr. After reaction completed, the mixture was distillated to remove MeOH, added with toluene and distilled again to give 5.2 g oil of methyl 3-methoxy-4-hydroxy cinnamate. 100 mL of toluene, 50 mL acetone and silver oxide (Ag₂O) were added to oil solution in the dark condition. The mixture was stirred for overnight. After reaction completed, the mixture was filtered to remove solid. The filtrate was distilled to give an oil and it was chromatographed on silica gel to give 0.8 g yellow solid of methyl 3-[2-(4-hydroxy-3-methoxyphenyl)-7-methoxy-3-(methoxycarbonyl)-2,3-dihydro -1-benzofuran-5-yl]prop-2-enoate.

MS (TOF): 415(M+H)⁺

¹H-NMR(CDCl₃, 400 Hz)δ: 7.63(1H, d, J=16 Hz, 8'-H), 7.18(1H, s, 2'-H), 7.02(1H, d, J=1.2 Hz, 6'-H), 6.90(3H, m, 2;5;6-H), 6.30(1H, d, J=16 Hz, 7'-H), 6.10(1H, d, J=8.4 Hz, 7-H), 4.32(1H, d, J=8.4 Hz, 8-H), 3.92(3H, OMe), 3.87(3H, OMe),3.83(3H, OMe), 3.80(3H, OMe).

3.5 g of methyl 3-[2-(4-hydroxy-3-methoxyphenyl)-7-methoxy-3-(methoxycarbonyl) -2,3-dihydro-1-benzofuran-5-yl]prop-2-enoate, 4.4 g of K₂CO₃ (4.4 g) and 40 mL of acetone were mixed and stirred. Then, dimethyl sulfate ((CH₃)₂SO₄) was added to the mixture and heated to reflux for 8 hr. After reaction completed, the reaction mixture was cooled to ambient temperature, 40 mL of water was added and stirred for 30 min. 100 mL of EA was added to solution and stirred for 30 min. After phase separation, the organic layer was separated, washed with brine, added with MgSO₄, and stirred for 30 min. After filteration to remove MgSO₄, the filtrate was distilled and purified by chromatography on silica gel column to give 0.58 g white solid of methyl 3-[2-(3,4-dimetoxyphenyl)-7-methoxy-3-(methoxycarbonyl)-2,3-dihydro-1-benzofuran-5-yl]prop-2-enoate.

MS (TOF): 429(M+H)⁺, 857(2M+H)⁺, 879(2M+Na)⁺

¹H-NMR(CDCl₃, 400 Hz)δ: 7.68(1H, d, J=16 Hz, 8'-H), 7.18(1H, s, 2'-H), 7.00(1H, d, J=1.2 Hz, 6'-H), 6.78(3H, m, 2;5;6-H), 6.28(1H, d, J=16 Hz, 7'-H), 6.06(1H, d, J=8.4 Hz, 7-H), 4.26(1H, d, J=8.4 Hz, 8-H), 3.92;3.85;3.82;3.80(15H, OMe)

1 g of methyl 3-[2-(3,4-dimetoxyphenyl)-7-methoxy-3-methoxycarbonyl-2,3-dihydro -1-benzofuran-5-yl]prop-2-enoate, 10 mL of acetone and 2.5 mL of water were mixed and stirred to dissolve. Then, 3% NaOH (6 mL) was added to the mixture and stirred for 0.5 hr. After reaction completed, the mixture was acidified and purified by chromatography on silica gel column with a 1:2:0.8 V/V mixture of petroleum ether, ethyl acetate and acetic acid as eluent. After removing solvent, it gave 1.5 g yellow solid of 5-[(E)-2-carboxyethenyl]-2-(3,4-dimetoxyphenyl)-2,3-dihydro-7-methoxy-3-benzofurancarboxylic acid (IM2).

MS (TOF): 423(M+Na)⁺, 823(2M+Na)⁺

EXAMPLE 3

Example 3 illustrates process of making a common intermediate IM3 for making compounds A and C in accordance with embodiments of the present invention.

Conversion of 2-amino-3(3,4-dimethoxyphenyl)propanic acid hydrochloride to IM3

Scheme 3:

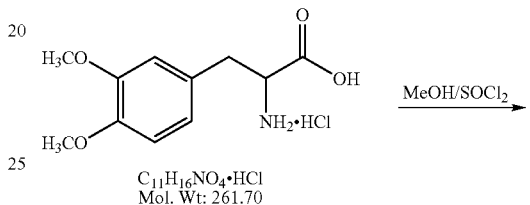

C₁₁H₁₆NO₄·HCl
Mol. Wt: 261.70

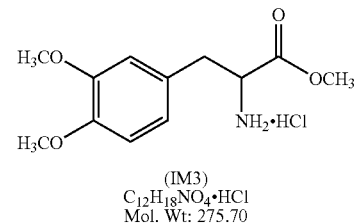

(IM3)
C₁₂H₁₈NO₄·HCl
Mol. Wt: 275.70

5.2 g of 2-amino-3-(3,4-dimethoxyphenyl)propanic acid hydrochloride and 50 mL of methanol (MeOH) were mixed and stirred for dissolution. Then, 2 mL of thionyl chloride (SOCl₂) was slowly dropped to the mixture within 5 min. The mixture was heated to reflux and stirred under refluxing for 2 hr. After reaction completed, the mixture solution is cooled and distilled to remove MeOH to give white solid. The solid and 50 mL of water were mixed and stirred to dissolve. The solution was cooled in ice bath and adjusted pH to ~10 with NH₄OH. The stirred solution mixture was extracted twice with CHCl₃. The organic layers are combined, added with magnesium sulfate, stirred and filtered to remove solid. The filtrate is distilled to give yellow oil. The yellow oil was crystallized with 10 mL of petroleum ether: THF (1:1) to give white solid of methyl 2-amino-3-(3,4-dimethoxyphynyl)propanate hydrochloride, IM3 (35 mg) with melting point 110-112° C.

¹H-NMR(CDCl₃, 400 Hz)δ: 6.89(1H, s, 2-H), 6.80(1H, d, J=8.0 Hz, 6-H), 6.77(1H, d, J=8.4 Hz, 5-H), 4.39(1H, t, J=5.6 Hz, 8-H), 3.86(3H, OMe), 3.81(3H, OMe), 3.71(3H, OMe), 3.40-3.28(2H, m, 7-H)

EXAMPLE 4

Conversion of IM1 to Compound A

Scheme 4:

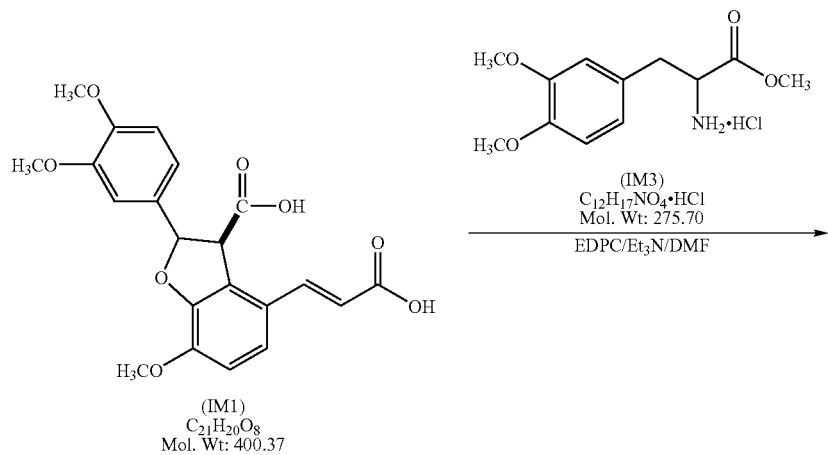

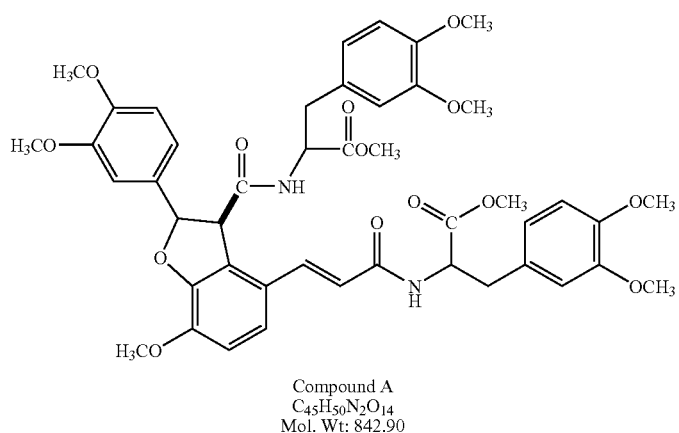

The chemical name of Compound A is: 2-(3,4-dimethoxyphenyl)-7-methoxy-4-{(E)-2-[1-(methoxycarbonyl)-2-(3,4-dimethoxyphenyl)-ethylcarbamoyl]-vinyl}-2,3-dihydro-benzofuran-3-carboxylic acid-1-(methoxycarbonyl)-[2-(3,4-dimethoxyphenyl)-ethyl]-amide.

33 mg of IM1 in 1.5 mL of dimethylformamide (DMF) and 50 mg of IM3 in 10 mL of DMF were mixed and stirred to dissolve. The mixture was cooled to 0° C. 31.8 mg of 1-piperazole carboyl chloride (DEPC) in DMF (0.5 mL) was slowly charged to the mixture at 0° C. Then, 36.7 mg of triethylamine ($Et_3N$) in 0.5 mL of DMF was slowly added to the mixture at 0° C. and stirred at 0° C. for 30 min. The solution mixture was warmed to ambient temperature and stirred for overnight. After reaction completed, the solution was distillated and purified to give 36 mg yellow solid of Compound A with melting point 174-176° C.

MS (TOF): 865(M+Na)$^+$, 1707(2M+Na)$^+$ $^1$H-NMR(CDCl$_3$, 400 Hz)δ: 7.39(1H, H-α'), 7.09-6.66 (5H, m), 6.59-6.11(6H, m), 5.88-5.78(2H, m, H-β',H-α), 4.95-4.76(2H, m, H-β",H-β'''), 4.24(1H, m, H-β), 3.95-3.67 (27H, OMe), 3.15-2.98(4H, m, H-α", H-α''')

EXAMPLE 5

Conversion of IM1 to Compound B

Scheme 5:

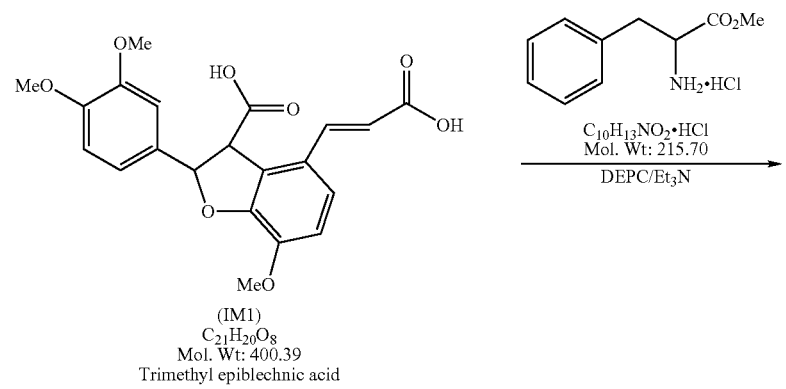

(IM1)
$C_{21}H_{20}O_8$
Mol. Wt: 400.39
Trimethyl epiblechnic acid

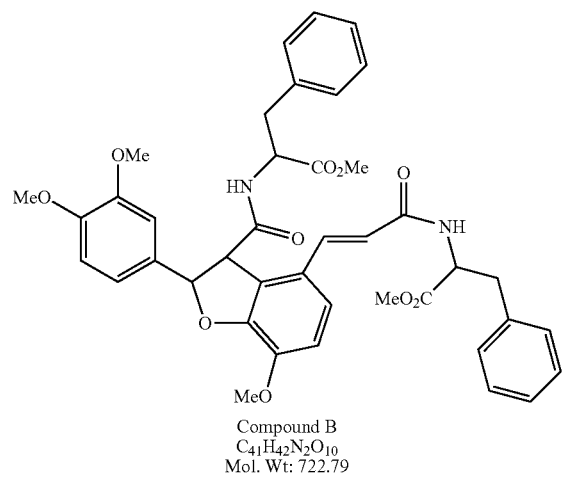

Compound B
$C_{41}H_{42}N_2O_{10}$
Mol. Wt: 722.79

The chemical name of Compound B is: 2-(3,4-dimethoxyphenyl)-7-methoxy-4-{(E)-2-[1-(methoxycarbonyl)-2-phenyl-ethylcarbamoyl]-vinyl}-2,3-dihydro-benzofuran-3-carboxylic acid-1(methoxycarbonyl)-[2-(3,4-dimethoxyphenyl)-ethyl]-amide.

50 mg of IM1, 178 mg of methyl 2-amino-3-phynylpropanate hydrochloride in 10 mL of DMF were mixed and stirred to dissolve. The solution mixture was cooled to 0° C. 145 mg of DEPC in 0.5 mL of DMF was slowly dropped to the solution mixture at 0° C. Then, 167 mg of triethylamine ($Et_3N$) in 0.5 mL of DMF was slowly dropped to the mixture at 0° C. and stirred for 30 min. The mixture was warmed to ambient temperature and stirred for overnight. After reaction completed, the solution was concentrated, purified by chromatography on silica gel to give an oil. It is crystallized from petroleum ether: EA to give 40 mg of yellow solid of Compound B with melting point: 202-204° C.

MS(TOF): 745(M+Na)$^+$, 1467(2M+Na)$^+$ $^1$H-NMR(CDCl$_3$, 400 Hz)δ: 7.75-6.25(15H, m), 6.42-6.48 (2H, m), 6.20(1H, d, J=7.6 Hz, H-α'), 5.76(1H, d, J=11.6 Hz,H-β'), 5.57(1H, d, J=6.0 Hz, H-α), 4.83-4.75(2H, m, H-β", H-β'"), 4.07(1H, m, H-β), 3.91;3.82;3.66;3.57(15H, OMe), 3.13-2.86 (4H, m, H-α", H-α'")

EXAMPLE 6

Example 6 shows process of making Compound C by conversion of IM2 to Compound C in accordance with an embodiment of the present invention.

Scheme 6:

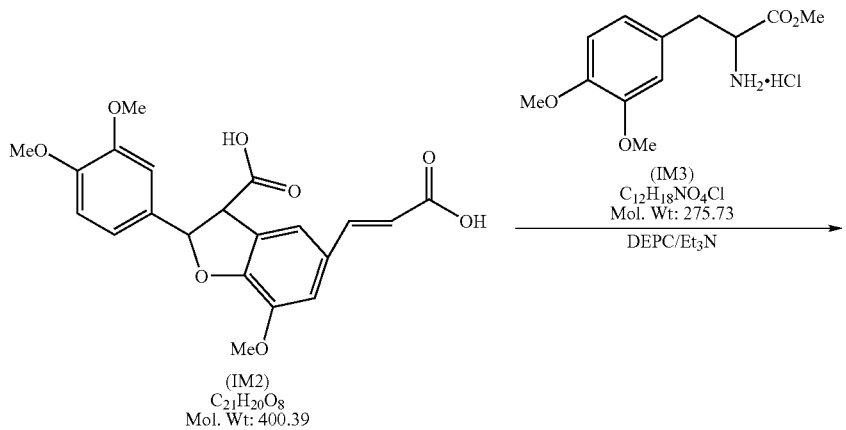

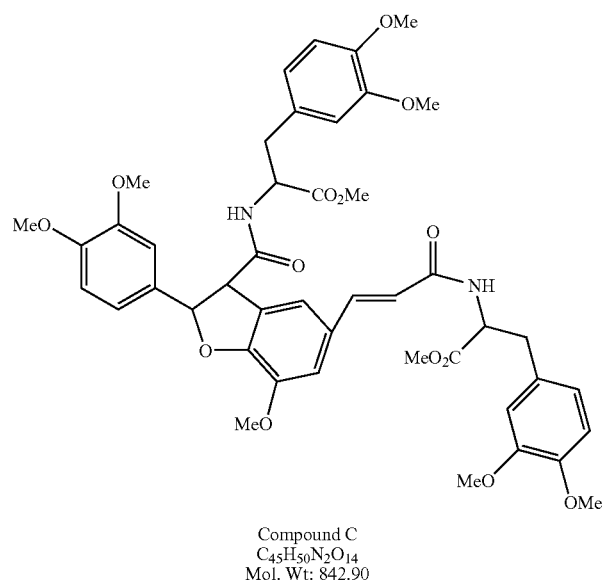

Compound C
C₄₅H₅₀N₂O₁₄
Mol. Wt: 842.90

The chemical name of Compound C is 2-(3,4-dimethoxyphenyl)-7-methoxy-5-{(E)-2-[1-(methoxycarbonyl)-2-(3,4-dimethoxyphenyl)-ethylcarbamoyl]-vinyl}-2,3-dihydro-benzofuran-3-carboxylic acid-1-(methoxycarbonyl)-[2-(3,4-dimethoxyphenyl)-ethyl]-amide.

57 mg of IM2, 89 mg of IM3, and 10 mL of DMF were mixed and stirred to dissolve. Then, 57 mg of DEPC and 66 mg of Et₃N (66 mg) were added to the mixture and stirred at ambient temperature for 15 hr. After reaction completed, the solution was distilled and purified by preparative thin layer chromatography to give yellow solid of Compound C (28 mg) with melting point 184-186° C.

MS (TOF): 865(M+Na)⁺, 881(M+K)⁺, 1707(2M+Na)⁺

1H-NMR (CDCl3, 400 Hz)δ: 7.50(1H, H-α'), 6.93-6.40 (12H, m), 6.16-6.02(2H, m), 5.90(1H, m), 4.98-4.88(2H, m, H-β'', H-β'''), 4.08(1H, m, H-β), 3.90-3.67(27H, OMe), 3.24-2.92(4H, m, H-α'', H-α''')

EXAMPLE 7

Example 7 shows process of making Compound C by conversion of IM2 to Compound D in accordance with an embodiment of the present invention.

Scheme 7:

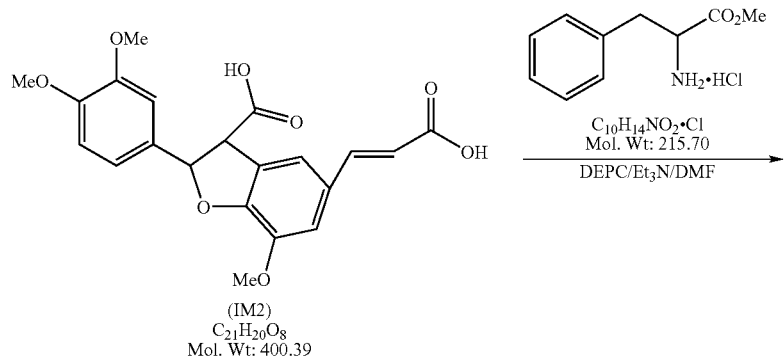

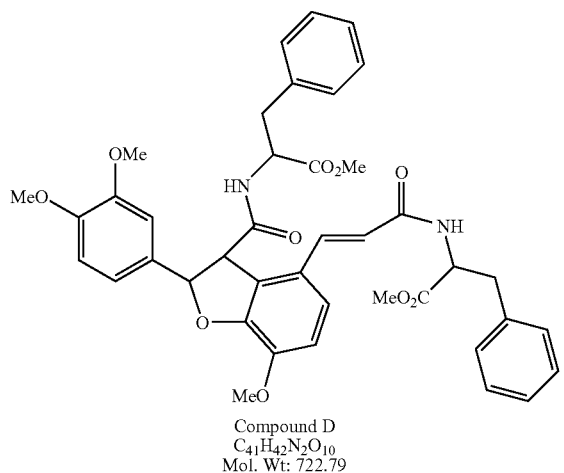

The chemical name of Compound D is 2-(3,4-dimethoxyphenyl)-7-methoxy-5{(E)-2-[1-(methoxycarbonyl )-2-(phenyl)-ethylcarbamoyl]-vinyl}-2,3-dihydro-benzofuran-3-carboxylic acid 1-(methoxycarbonyl)-2-(phenyl)-ethylamide 50 mg of IM2, 54 mg of methyl 2-amino-3-phynylpropanate hydrochloride, and 10 mL of DMF were mixed and stirred to dissolve. Then, the solution mixture was cooled to 0° C., 50 mg of DEPC in 0.5 mL of DMF was slowly dropped to the mixture at 0° C., 60 mg of Et$_3$N in 0.5 mL of DMF (0.5 mL) was added slowly, and stirred at 0° C. for 30 min. The reaction mixture was warmed to ambient temperature and stirred for overnight. After reaction completed, the solution mixture was distilled and isolated by preparative thin layer chromatography to give 33 mg yellow solid of Compound D with melting point 222-224° C.

MS (TOF): 745(M+Na)$^+$, 1467(2M+Na)$^+$ $^1$H-NMR (CDCl$_3$, 400 Hz)δ; 7.52(1H, m, H-α'), 7.30-6.74 (15H, m), 6.23-6.12(2H, m), 6.07(1H, d, J=7.2 Hz, H-β'), 5.95(1H, d, J=7.2, H-α), 5.07-4.94(2H, dd, J=38;4.0 Hz, H-β"; H-β'''), 4.16-4.10(1H, m, H-β), 3.95-3.69(15H, OMe), 3.30-3.06(4H, m, H-α";H-α''')

EXAMPLE 8

Example 8 shows process of making Compound C by conversion of IM2 to Compound E in accordance with an embodiment of the present invention Scheme 8:

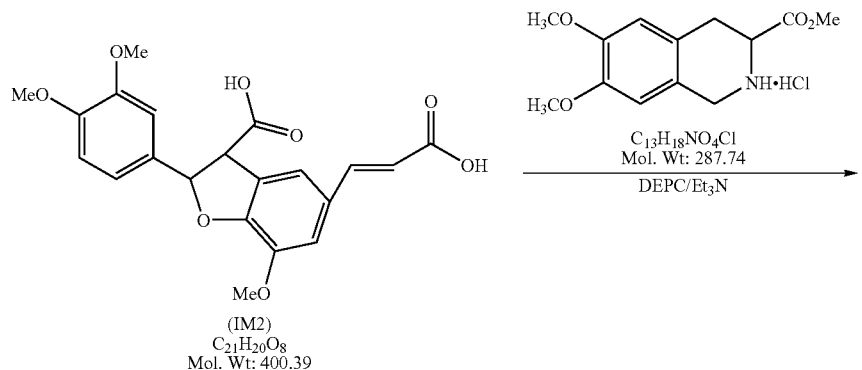

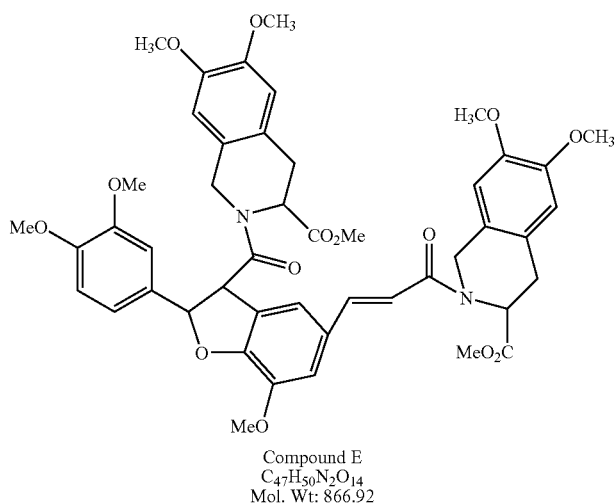

The chemical name of Compound E is 2-(3,4-dimethoxyphenyl)-7-methoxy-3-[carbonyl-(6,7-dimethoxy-3-methoxycarbonyl-1,2,3,4-tetrahydroisoquinoline)]-5-{-2-[-carbonyl-6,7-dimethoxy)-3-(methoxycarbonyl)-1,2,3,4-tetrahydroisoquinoline) vinyl}-2,3-dihydro-benzofuran.

68 mg of IM2, 100 mg of 6,7-dimethoxy-3-carbomethyl-1,2,3,4-tetrahydro isoquinoline hydrochloride and 10 mL of DMF were mixed and stirred to dissolve. The mixture was cooled to 0° C., added with 70 mg of DEPC in 0.5 mL of DMF (0.5 mL) and 80 mg of Et₃N in 0.5 mL of DMF and stirred at 0° C. for 30 min. The mixture was warmed to ambient temperature and stirred overnight. After reaction completed, the mixture was distilled and purified by TLC (Rf=0.36) to give yellow solution. The solution was concentrated to give 45 mg of yellow solid as Compound E with melting point: 208-210° C.

MS (TOF): 889(M+Na)⁺, 1755 (2M+Na)⁺

¹H-NMR (CDCl₃, 400 Hz)δ: 7.72(1H, H-α'), 7.20-6.43 (10H, m), 6.30(1H, d, J=8.0 Hz, H-β'), 5.99-5.89(1H, m, H-α), 5.64(1H, s), 5.35(1H, s), 3.86-3.58(27H, OMe), 3.24-3.06(4H, m), 2.94-2.82(2H, m), 2.13-2.07(2H, m)

EXAMPLE 9

Example 9 shows process of making Compound C by conversion of IM2 to Compound F in accordance with an embodiment of the present invention Scheme 9:

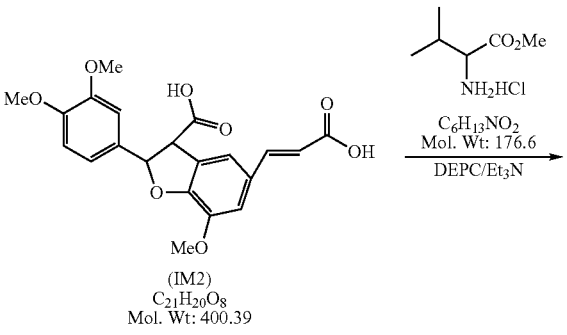

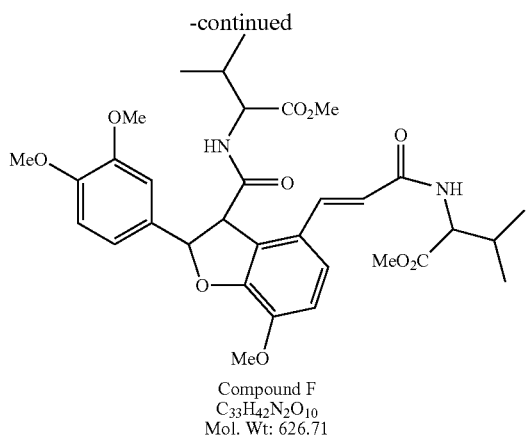

Compound F
C₃₃H₄₂N₂O₁₀
Mol. Wt: 626.71

The chemical name of Compound F is 2-(3,4-dimethoxyphenyl)-7-methoxy-5-{(E)-2-[1-(methylcarbonyl)-2-methyl-propyylcarbamoyl]-vinyl}-2,3-dihydro-benzofuran-3-carboxylic acid-1(methyl-carbonyl)-2-(methylpropyl)-amide.

207 mg of IM2, 191 mg of methyl 2-amino-3-methylbutanoate hydrochloride, and 10 mL of DMF were mixed and stirred to dissolve. Then, 199.5 mg of DEPC and 230 mg of Et₃N were added to the reaction mixture and stirred at ambient temperature for 15 hr. After reaction completed, the solution mixture was distilled and isolated by preparative thin layer chromatography to give 57 mg yellow solid of compound F with melting point: 154-156° C.

MS(TOF): 627(M+H)⁺, 649 (M+Na)⁺, 665(M+K)⁺, 1275 (2M+Na)⁺

¹H-NMR(CDCl₃, 400 Hz)δ: 7.59-7.53(1H, H-α'), 7.13-6.82(5H, m), 6.40 6.30(2H, m), 6.15(1H, H-β'), 6.02(1H, H-α'), 4.71-4.58(2H, dd, J=8.4; 4.8 Hz,H-β", H-β'''), 4.23 (1H, m, H-β), 3.94-3.69(15H, OMe), 2.24-2.15(2H, m, H-α", H-α'''), 0.99-0.87(12H, Me)

II. Utilities of the Compounds in Accordance with Embodiments of the Present Invention The inventors have discovered that Sal-B analogs in accordance with the present invention possess the ability to reduce cellular hypertrophy via regulating the expression of ETAR. In addition, the inventors have also discovered that endothelin receptors involve in the ability for cancer cells adhering to human umbilical vein endothelial cells (HUVECs) and to cross the layer of endothelial cells, which contributes to tumor metastasis. The inventors have also discovered that treating A10 smooth muscle cells with Sal-B and its analogs can reduce the expression levels of ETAR mRNA and protein. Analyzing the expression levels of ETAR mRNA in prostate cancer cells (PC-3), breast cancer cells (MCF-7), and nasopharyngeal cancer cells (Hone-1) reveals that PC-3 and MCF-7 cells do express ETAR mRNA. It was found that to treat MCF-7 cells with Sal-B and EBA can reduce the expression of ETAR mRNA. Furthermore, Sal-B, compound B, and compound A can significantly inhibit the growth of PC-3 and Hone-1 cells, and Sal-B can significantly induce the apoptosis of PC-3 cells. Sal-B can therefore significantly inhibit the growth of prostate cancer cells. The present invention has shown that Sal-B and its analogs possess the ability to reduce vascular smooth muscle cell hypertrophy and lessen the expression of ETAR in MCF-7 cells. In addition, these analogs can inhibit the metastasis of breast cancer cells and inhibit the growth of prostate and nasopharyngeal cancers. Therefore, the Sal-B analogs disclosed by the present invention can be used to treat diseases in relation to the overexpressions of endothelin 1 or endothelin receptors. The said diseases include tumor growth and metastasis, as well as cardiovascular diseases, e.g. hypertension, atherosclerosis, and myocardial infarction.

The interaction between endothelin and endothelin receptors (ET/ETRs) can affect the downstream signaling pathways between MCF-7 cells or nasopharyngeal carcinoma cells (NPC-TW01) and human umbilical vein endothelial cells (HUVECs), and then inhibit cancer cells chemotaxis, adhesion between cancer cells and endothelial cells, and tumor metastasis via crossing the layer of endothelial cells. Since Sal-B can significantly reduce hypertension and inhibit vascular smooth muscle cell hypertrophy, and may be able to reduce cancer metastasis, its analogs should be able to provide similar therapeutic effects. It is found that treating MCF-7 cells with Sal-B's derivative-EBA can reduce ETAR mRNA expression, which indicates that EBA may be able to inhibit breast cancer cells chemotaxis, adhesion between breast cancer cells and endothelial cells, and tumor metastasis via crossing the layer of endothelial cells. The present invention has verified that Sal-B can inhibit the growth of PC-3 and Hone-1 cells, and induce apoptosis in PC-3 cells. In addition, the analog Compound B and Compound A are also able to inhibit the growth of PC-3 cells. These results suggest that the Sal-B's analogs, Compound B and Compound A, may cause cells to undergo apoptosis via inducing mitotic arrest or inhibiting COX-2 protein expression. Therefore, Sal-B's analogs, particularly Compounds B and A, can be used as the anti-cancer drugs.

Examples 10 to 15 below describes material, test, and analytical method used in the Examples 16 to 22 study the utilities of the compounds in accordance with embodiments of the present invention.

EXAMPLE 10

Cell Culture
(1) Culture of Rat Thoracic Aorta Smooth Muscle Cells

Four-week old WKY (Wistar-Kyoto Rat) and SHR (spontaneous hypertensive rat) rats were selected. After injecting sodium pentobarbital (50 mg/kg) into the abdominal cavity of the rats for anesthesia, the rats' abdominal and thoracic cavities were opened using surgical implements and then the thoracic aorta of the diaphragm was removed and placed in DMEM medium. After cleaning off the surrounding connective tissue, fat, and blood clots, the aorta was placed in digestion buffer (2 mg/ml Collagenase type I, 125 µg/ml Elastase type 1, 375 ug/ml trypsin inhibitor, 2 mg/ml BSA), and placed in an incubator for approximately 10 -20 minutes (37° C., 5% CO₂). The outer membrane (tunica adventitia) was removed from the blood vessel in order to obtain the pure middle layer of vascular tissue. The vascular tissue was placed in fresh digestion buffer, and then cut into pieces approximately 1 mm² in size. These were then placed in an incubator for roughly 2 hours (37 C, 5% CO₂). After dispersing the pieces of tissue, more culture medium was added (DMEM, 10% FBS, 5% Penicillin/Streptomycin) to terminate the enzymatic reaction. The resulting mixtures were placed in a centrifuge at 1,000 rpm for 10 min. to remove the supernatant liquid, and then the cells were suspended in culture medium and cultured in an incubator (37 C, 5% CO₂). The culture medium was replaced every two days, and subcultures were made regularly.

(2) Culture of Cell Lines

PC-3 and Hone-1 cells were placed in culture medium (DMEM, 10% FBS, 5% Penicillin/Streptomycin, 3.7 g/L sodium bicarbonate, 2.89 g/L HEPES), MCF-7 cells were placed in culture medium (MEM, 10% FBS, 5% Penicillin/Streptomycin, 2 mM L-glutamine, 1.5 g/L sodium bicarbonate, 0.1 mM non-essential amino acids, 1 mM sodium pyruvate), and A1N4 cells were placed in culture medium (IMEM, 0.5% FBS, 5% Penicillin/Streptomycin, 5 μg/L Hydrocortisone, 0.9 μM insulin, 10 μg/L EGF), and all were cultured in an incubator (37° C., 5% CO2). The culture medium was replaced every two to three days, and subcultures were made regularly.

EXAMPLE 11

Cell Subcultures

Subcultures were made when the cells had covered the bottom of a culture dish. After removing the culture medium, PBS buffer (137 mM NaCl, 2.7 mM KCl, 2 mM $KH_2PO_4$, 10 mM $Na_2HPO_4$) was used to wash the bottom of the culture dish three times, and the cells were treated with 0.05% Trypsin-EDTA for 3-5 min. (37° C.). After the cells had mostly separated from the bottom of the culture dish, the dish was gently tapped to suspend the cells in the Trypsin-EDTA solution. An additional 10 ml of culture medium was added to neutralize the Trypsin, and clumps of cells were dispersed by rinsing. The resulting mixtures were placed in 15 ml centrifuge tubes and subjected to centrifugation at a 1,000 rpm for 10 min. The supernatant liquid was removed and fresh culture medium was added to re-suspend the cells. The cells were then transferred to new culture dishes in a ratio of 1:2-1:3.

EXAMPLE 12

The Purity Identification of Rat Thoracic Aorta Smooth Muscle Cells

After culturing rat (WKY and SHR) thoracic aorta smooth muscle cells to a certain density (approximately 50%-70% full), the purity of the vascular smooth muscle cells was identified. After removing the culture medium from the dishes and rinsing the cells with PBS, 2% formaldehyde (in PBS) was added to fix the cells at room temperature for 30 minutes. The cells were then soaked in 0.5% triton-X-100 (in PBS) three times, for 20 minutes each time. The cells were treated with anti-smooth muscle-α-actin primary antibody (diluted to 1:40, in PBS) at 37° C. for 1 hour. After the primary antibody treatment, the cells were soaked in 0.5% triton-X-100 (dissolved in PBS) three times, for 20 minutes each time, to wash out the residual antibody. The cells were treated with goat anti-mouse-FITC secondary antibody (diluted to 1:80, dissolved in PBS) at 37° C. for 1 hour in darkness. After the secondary antibody treatment, the cells were soaked in PBS three times, for 10 minutes each time, and soaked in 0.9% NaCl (in PBS) for 10 minutes. The cells were treated with DAPI (1 μg/ml, in PBS) at room temperature for 10 minutes to stain the cell nuclei. Using fluorescence microscope to observe and record the cell staining.

EXAMPLE 13

MTT Test

The cells ($1 \times 10^5$ cells/well in 24-well plates) were cultured for 24 hrs. Different concentrations of Sal-B and its analogs (0, 50, 100, 150, 200, 250 μg/ml) were added to treat the cells. After treating for 48 hrs, 100 μl MTT solution was added to each well, and the plate was placed in an incubator for 1-4 hrs. After adding 400 μl DMSO to treat the cells for 30 min., 200 μl samples were collected and placed in a 96-well plate to conduct the absorption measurement at 550 nm.

EXAMPLE 13

Western Blot Analysis

The smooth muscle cells ($5 \times 10^5$ cells in 35 mm culture dish) were treated with Sal-B and its analogs for 48 hrs, and then a proteinase inhibitor solution was used to collect proteins from the cells.

Protein Concentration Analysis:

The protein concentrations in the samples were calculated by using BSA as the standards to construct a standard curve. After mixing Bradford Protein assay reagent evenly with the standards or the samples, the OD595 absorption values were measured. Standard curve was constructed by plotting OD595 values of the BSA standards versus their concentrations. The protein concentrations of the samples were calculated from the standard curve.

SDS-Polyacrylamide Gel Electrophoresis:

Bio-Rad's Mini-Protean III Dual Slab Cell instrument was used. A 12% polyacrylamide separating gel solution was prepared and placed into a electrophoretic gel preparation device. Deionized water was added to flat the surface of the separating gel solution, and the water was poured off after the gel had coagulated. A stacking gel solution containing 5% polyacrylamide was added and then a comb was inserted. The comb was removed after the stacking gel had coagulated, and the gel was placed into an upright electrophoresis tank. A suitable amount of running buffer was added, and then the protein samples were loaded into the wells of stacking gel layer. For stacking gel layer, gel electrophoresis was performed for 10 min at a voltage of 90 V. Then, for separating gel layer, gel electrophoresis was performed for roughly 1.5 hrs at a voltage of 150 V. After gel electrophoresis was finished, the gel was removed and stained with Coomassie brilliant Blue R250 for 15 min. After that, the destain buffer was used to remove the background color. The gel was covered with cellophane and air dried for preservation.

Antibody Hybrid:

The Bio-Rad's Mini-Protean III system protein transfer equipment was used. After soaking the PVDF membrane in methanol to activate it, the membrane was soaked in transfer buffer at 4° C. The proteins containing in the gel obtained from gel electrophoresis was transferred to the PVDF membrane under a 400 mA current at 4° C. for 1 hour. After the transfer, the PVDF membrane was removed and shaken in blocking solution for 1 hour, and then treated with the primary antibodies of anti-ETAR, anti-ETBR, and anti-smooth muscle-α-actin for 1 hour, and washed with PBST three times, for 5 min. each time. After that, the membrane was treated with goat anti-rabbit-HRP secondary antibody for 1 hour, and then the membrane was washed with PBST three times, for 15 min. each time. Then, the membrane was treated with the developer, Western Lightning Reagent, for 3 min., after which the membrane could be developed by using Kodak BioMax light film.

EXAMPLE 14

Real-Time Quantitative RT-PCR

Extraction of cellular RNA: Subculturing smooth muscle cells to 100-mm culture dishes. After the cells had filled the culture dishes, Sal-B and its analogs were added to treat the cells for 48 hrs. After that, 1×PBS solutions were added to wash the cells three times. After adding 1 ml TRIzol, the cells were scraped off and placed in 1.5 ml micro-centrifuge tubes. Following the addition of 0.2 ml chloroform to each tube, the tubes were shaken, left at room temperature for 3 min., and run in a centrifuge at 12,000 rpm for 15 min. The supernatant liquid was removed and the cells placed in new micro-centrifuge tubes. After adding an amount of isopropyl alcohol equivalent to one-half of the volume of the supernatant liquid, and mixing until homogeneous, the samples were allowed to stand at room temperature for 10 min. The supernatant liquid was removed after centrifugation at 12,000 rpm for 10 min. 1 ml 70% alcohol was added to wash out salts, followed by centrifugation for 5 min. and removal of supernatant liquid. The samples were dissolved in 50 µl DEPC-$H_2O$ after drying.

(1) cDNA synthesis: 1 µl Random hexamer primer (20 µM) and 1 µl dNTP(10 mm) were added to 3 µg RNA, which was allowed to react at 65° C. for 5 min., and then placed on ice promptly. After the addition of 2 µl 10× reaction buffer, 0.5 µl RNaseOUT (40 unit/µl) and 1 µl SuperScript III RT (200 unit/µl), the solution was mixed until homogeneous, and allowed to react at 50° C. for 50 min. After that, the mixture was heated to 85° C. for 5 min. to terminate the enzymatic reaction. The samples were preserved at −70° C. for later use.

(2) PCR quantitative analysis: After adding 7.5 µl PCR primer mix (400 nm each) and 15 µl SYBR Green dye reagent to the 7.5 µl cDNA template, the solution was placed in Bio-Rad's iCycler for PCR reaction. The resulting data was inputted into Gene Expression Analysis for iCycler iQ Real-Time PCR Detection System for quantitative analysis of gene expression.

EXAMPLE 15

Flow Cytometry

After suspending cells, the precooled 70% ethanol was used for fixing the cells. After centrifuging the mixture for 10 min. at 3,000 rpm, supernatant liquid was removed. Propidium iodide (PI) buffer (0.1% Triton X-100, 0.2 µg/ml RNase A, 40 µg/ml PI) was added, and then the solution was kept still at 37° C. for 30 min. After that, the cell cycle analysis was conducted by flow cytometry.

Examples 16-19 show the cytotoxicity of Sal-B and its analogs.

EXAMPLE 16

Normal Cells (A10) were Treated with Sal-B and EBA

Cell viability testing (MTT testing) was employed to determine the cytotoxicity of Sal-B and EBA to vascular smooth muscle cells. Vascular smooth muscle cells (cell line A10) were treated with Sal-B and EBA at concentrations of 0, 0.1, 0.2, 0.3, 0.4, and 0.5 mM. After treating for 48 hrs, MTT was added and allowed to react for 3 hrs at 37° C. Then, DMSO was added and allowed to react for 30 min., after that, the OD570 absorption values were measured. Cell viability was still 90% when the drug concentration reached 0.2 mM.

EXAMPLE 17

Cancer Cells were Treated with Sal-B and EBA

Cancer cells were treated with Sal-B and EBA at concentrations of 0, 0.1, 0.2, 0.3, 0.4, 0.5 mM. After treating for 48 hrs, MTT was added, and then allowed to react for 3 hrs at 37° C. After that, DMSO was added and allowed to react for 30 min., the OD570 absorption values were measured. Cell viability was above 80% when nasopharyngeal cancer cells (Hone-1) were treated with 0.05 mM Sal-B and EBA. However, when Hone-1 cells were treated with 0.1 mM and 0.2 mM Sal-B, the cell viability was reduced to approximately 60%. But the cell viability remained above 70% for treating with 0.1 mM and 0.2 mM EBA. Similar results were obtained when prostate cancer cells (PC-3) were treated with the drugs: Cell viability was above 80% for treating PC-3 cells with 0.2 mM Sal-B or EBA. When treating PC-3 cells with 0.3 mM (or higher) Sal-B, the cell viability was reduced. But treating with EBA of higher concentrations did not significantly reduce the cell viability. In addition, when treating breast cancer cells (MCF-7) with Sal-B or EBA, the different concentrations of Sal-B and EBA have no significant effect on cancer cell viability.

The results of drug cytotoxicity tests involving different cancer cell lines suggest that Sal-B may be more toxic to nasopharyngeal cancer cells and prostate cancer cells than equivalent concentrations of EBA. Furthermore, when treating a normal mammary gland cell line (A1N4) with Sal-B and EBA, no significant difference was observed on the cytotoxicity results. This indicates that Sal-B and EBA have different cytotoxicity effects on cancer cells and normal cells. The results thus suggest that Sal-B may have a specific toxicity against nasopharyngeal and prostate cancer cells.

EXAMPLE 18

Normal Cells (A10) were Treated with Compounds A to F

Sal-B's analogs, compounds A to F, were dissolved in DMSO, and then added to A10 cells to observe the results. After treating with 0.2 mM analogs for 48 hrs, the samples treated with compounds B and E displayed significant precipitation, and the sample treated with compound A led to a high level of cell death.

EXAMPLE 19

Cancer Cells were Treated with Compounds A to F

MTT testing was employed to observe the viability of cancer cells after treating with Sal-B and the six synthetic analogs. The viability of prostate cancer cells (PC-3) was found to be reduced as the concentration of Sal-B was increased, and compounds B and A also led to the similar results. In contrast, the viability of prostate cancer cells (PC-3) did not be reduced as the concentrations of the other four compounds, C to F, were increased (FIG. 1).

Figure 2:
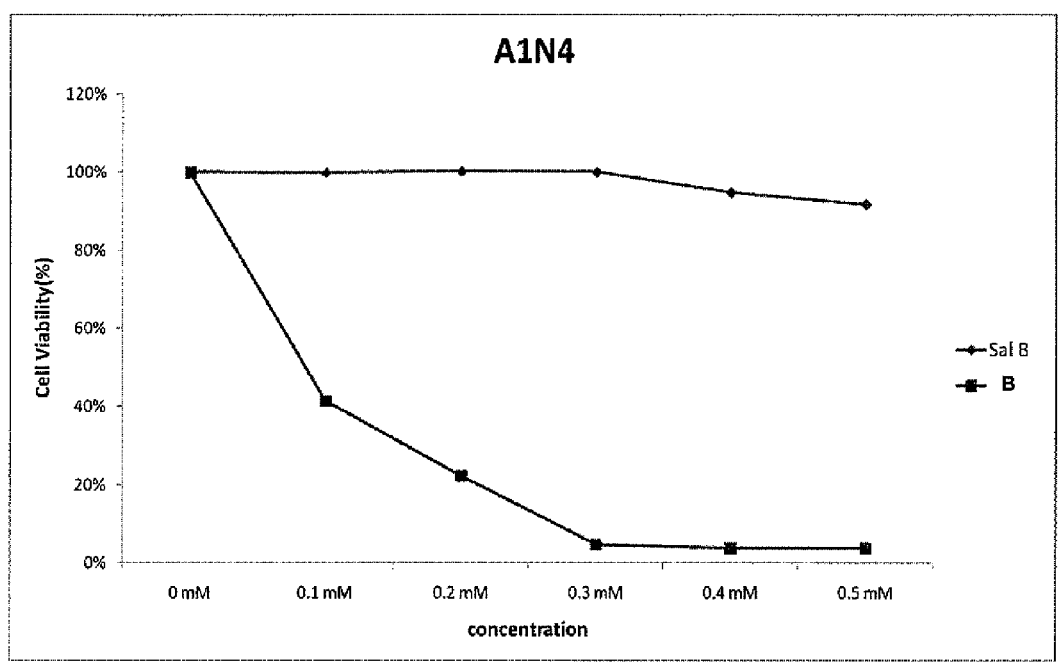
FIG. 2 illustrates the effects of Sal-B and Compound B on the viability of normal cells.

It can be inferred from the results of cytotoxicity tests involving cancer cell lines that Sal-B and compounds B and A have relatively high cytotoxicity against cancer cells. Further tests on normal mammary gland cells (A1N4) revealed that Sal-B is not highly toxic to normal cells, but compound B is relatively toxic to normal cells (FIG. 2).

Examples 20-22 show the ability of Sal-B and its analogs to reduce ETAR gene expression

EXAMPLE 20

Down-Regulating ETAR by Sal-B and EBA

For analysis of ETAR protein expression, 100 µg/ml of either Sal-B or EBA was added to treat vascular smooth muscle cells at full confluence 100-mm culture dishes for 48 hrs. Total protein was extracted from the cells, and the same concentrations of total protein were sampled. The Western blot method was conducted on the samples by using Anti-ETAR antibody. The results revealed that when treating the cells with Sal-B or EBA, the ETAR protein expression was significantly reduced as comparing with the control, which did not treated with Sal-B or EBA. In contrast, the ETBR protein expression did not be reduced during the analysis. This indicates that, while both Sal-B and EBA can effectively reduce ETAR protein expression, they have no effect on ETBR protein expression. It may therefore be concluded that Sal-B and EBA have specificity on down-regulating the ETAR protein/gene expression.

Furthermore, after treating vascular smooth muscle cells with 100 μg/ml of either Sal-B or EBA for 48 hrs, the identical concentrations of cellular whole RNA were sampled for the synthesis of cDNA by using reverse transcriptase. The PCR method was employed to determine the amounts of endothelin receptor mRNA expression. The results revealed that, when treating with Sal-B or EBA, the endothelin receptor mRNA expression was reduced as comparing with the control, no matter 25 or 30 reaction cycles were chosen. For the analysis of ETAR mRNA expression by using the real-time PCR method, vascular smooth muscle cells at full confluence 100-mm culture dishes were treated with 100 μg/ml of either Sal-B or EBA for 48 hrs. The identical concentrations of cellular whole RNA were sampled for the synthesis of cDNA by using reverse transcriptase. The real-time PCR method was used to compare the amounts of ETAR mRNA expression. The results revealed that when treating the cells with 100 μg/ml of Sal-B or EBA for 48 hrs, the ETAR mRNA expression was reduced as comparing with the control, in which, when treating with Sal-B, the mRNA expression was approximately 27% of that in the control, and while treating with EBA, the mRNA expression was roughly 51% of that in the control.

Figure 3:
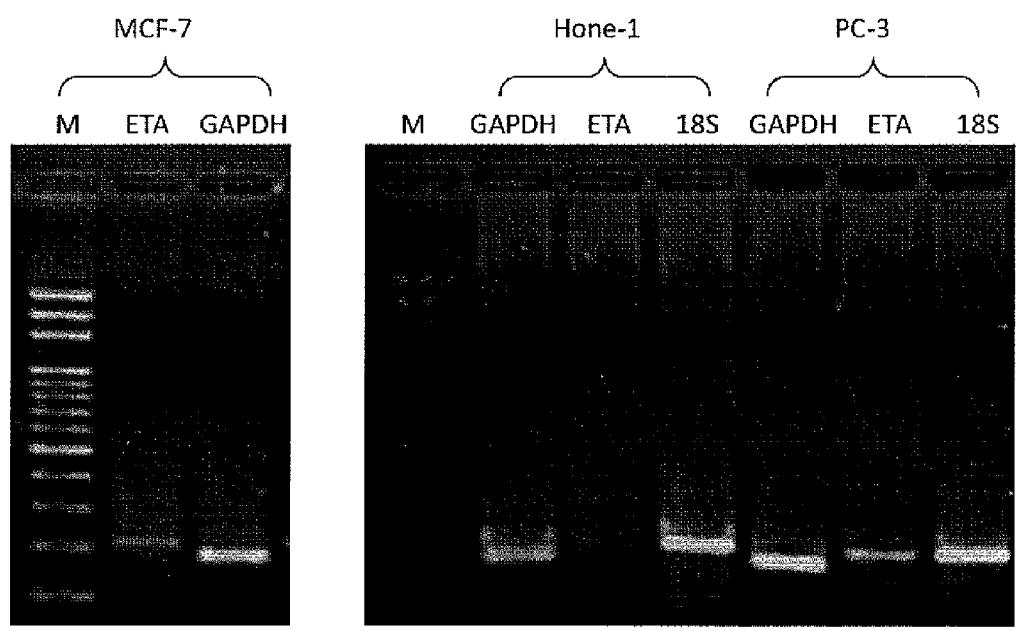
FIG. 3 illustrates ETA gene expression in the Hone-1, PC-3, and MCF-7 cell lines.

The PCR method was also used to observe ETA gene expression in the Hone-1, PC-3, and MCF-7 cell lines. While no ETAR mRNA expression was seen in nasopharyngeal cancer cells (Hone-1), significant ETAR gene expressions were observed in both PC-3 and MCF-7 cancer cells (FIG. 3). The latter two cell types were therefore used in further experiments.

PC-3 and MCF-7 cancer cells were treated with Sal-B and EBA for 48 hrs, and the identical concentrations of cellular whole RNA were sampled for the synthesis of cDNA by using reverse transcriptase. The PCR method was then used to compare the amounts of endothelin receptor mRNA expression. While the PC-3 cells were treated with either Sal-B or EBA, its ETAR gene expression was not reduced. However, when MCF-7 cells were treated with EBA, its ETAR gene expression was reduced significantly. This result suggests that drug treatment may cause a reduction in ETAR gene expression in MCF-7 breast cancer cells; therefore, MCF-7 cells may be suppressed by treating with Sal-B or EBA.

EXAMPLE 21

Down-Regulating ETAR by Compounds A to F

Figure 4:
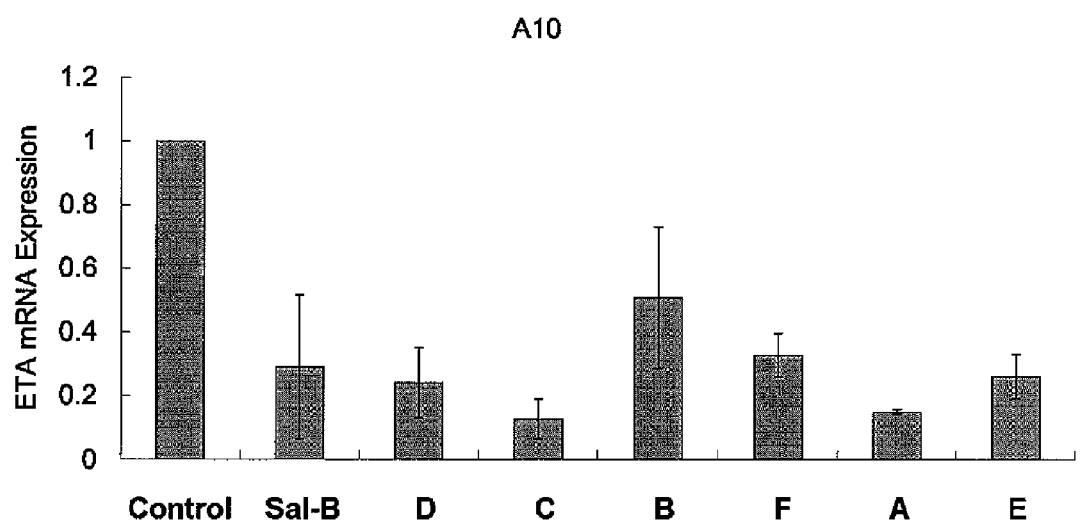
FIG. 4 illustrates the effects of Sal-B and Compounds A-F on down-regulating ETAR mRNA expression.

The different analogs, compounds A to F, had different effects on ETAR mRNA expression. The control group represented treating smooth muscle cells (A10) with DMSO, and the positive control group represented treating the cells with Sal-B. The smooth muscle cells were treated with 0.2 mM Sal-B and compounds A to F for 48 hrs. The identical concentrations of cellular RNA were sampled for the synthesis of cDNA by using reverse transcriptase. The real-time PCR method was employed to determine the amounts of ETAR mRNA expression. Compared with the control group, compound B had the least effect on down-regulating ETAR mRNA expression, as approximately 50% of the ETAR mRNA remained after the treatment. Compounds C and A had the greatest effect on down-regulating ETAR mRNA expression, with under 20% of ETAR mRNA remaining after the treatment. However, compound A also displayed relatively high cytotoxicity. The other drugs all led to less than 30% remaining ETAR mRNA, and their effects on down-regulating ETAR mRNA expression were similar to that of Sal-B (FIG. 4). Compounds A to F have the similar effect as Sal-B on down-regulating the ETAR mRNA expression of A10 cells. So, the ETAR mRNA over-expression related diseases may be suppressed by treating with compounds A to F.

EXAMPLE 22

Example 22 shows inducement of apoptosis in cancer cells by Sal-B and its analogs.

Figure 5:
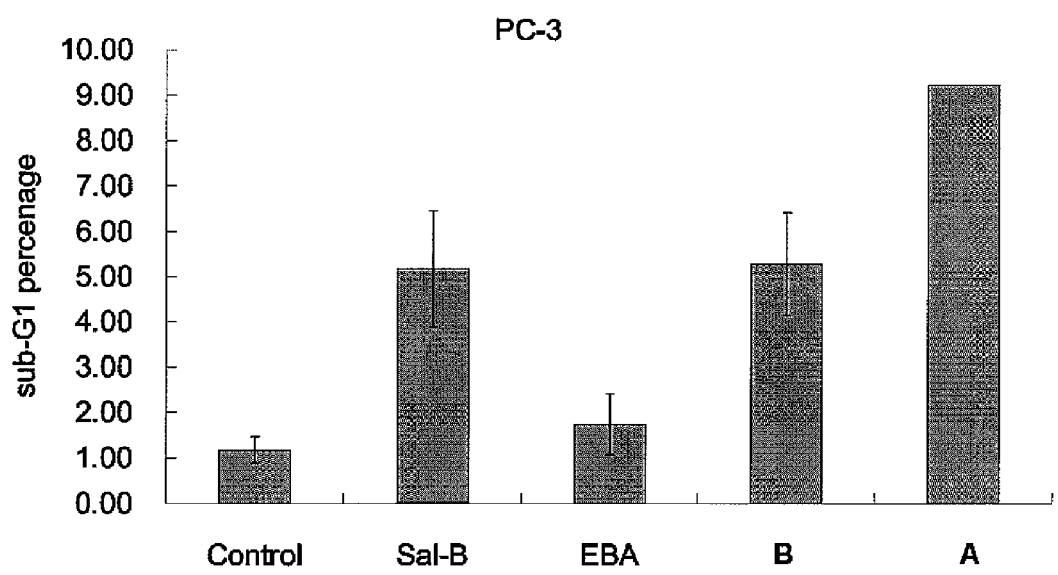
FIG. 5 illustrates the effects of Sal-B, EBA, and Compounds A-B in inducing the apoptosis of cancer cells.

Flow cytometry was used to determine whether Sal-B and its analogs induced apoptosis in cancer cells. After treating PC-3 cancer cells with 0.4 mM Sal-B and EBA, and 0.01 mM compounds B and A for 48 hrs, the cells were collected and allowed to react with PI buffer for 30 min. Flow cytometry was then employed to measure the cell cycle. Approximately 5.16% of PC-3 cancer cells were at sub-G1 phase after treating with Sal-B, roughly 5.27% were at sub-G1 phase after treating with compound B, and roughly 8.54% were at sub-G1 phase after treating with compound A. However, for the control, only around 1.18% of the cells were at sub-G1 phase. Therefore, Sal-B and its analogs (compounds B and A) thus caused a significant increase in the percentage of cells at sub-G1 phase. When EBA was used for treatment, however, only approximately 1.73% of PC-3 cells were at sub-G1 phase, which was not significantly different from the percentage in the control (FIG. 5). These results indicate that while Sal-B and compounds B and A can all induce the apoptosis of cancer cells, but EBA does not provide this effect.

Experimental results suggest that the drugs may down-regulate the ETAR gene expression in smooth muscle cells by increasing the degradation rate of the mRNA. According to some literatures, the increase of the degradation rate of the mRNA may be regulated by the AU-rich element (ARE) in the 3' untranslated region (3' UTR) of mRNA or microRNA (Chen, 1995; Iorio, 2008). Analysis of the ETAR mRNA 3'UTR sequence has shown the presence of ARE regions and microRNA binding sequences.

Because Sal-B's analogs, compounds A through F, are able to reduce cells' ETAR gene expression, they can be used to treat diseases linked with overexpression of ETAR/ET-1, such as cardiovascular diseases including hypertension, atherosclerosis, and myocardial infarction, and tumor growth and metastasis.

Compounds B and A have also been found to inhibit the growth of PC-3 cancer cells. In addition, compound A is ten times more toxic to PC-3 cells than Sal-B is, but has low toxicity to normal cells (A1N4). The Sal-B analogs, compounds B and A, may be able to induce mitotic arrest or inhibit COX-2 protein expression, which may lead to the apoptosis of cancer cells, therefore, the analogs can be used as anti-cancer drugs.

The invention is not limited by the embodiments described above which are presented as examples only but can be modified in various ways within the scope of protection defined by the appended patent claims.

We claim:

1. A compound of formula (I) or a salt thereof

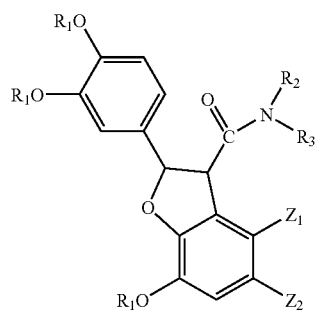

wherein

R$_1$ is C$_1$-C$_6$ alkyl, phenyl, benzyl, or a hydroxyl protecting group each of Z$_1$ and Z$_2$ is independently H or C=C—CO—NR$_2$R$_3$ optionally substituted with C$_1$-C$_6$ alkyl on the vinyl group with the proviso that one of Z$_1$ and Z$_2$ is H, and Z$_1$ and Z$_2$ are not H at the same time;

R$_2$ is H,

R$_3$ is

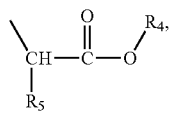

or R$_2$ and R$_3$ together form an optionally substituted 5-7 membered monocyclic ring or an optionally substituted 8-12 membered bicyclic ring;

R$_4$ is C$_1$-C$_6$ alkyl, allyl, phenyl, or benzyl; and

R$_5$ is C$_1$-C$_6$ alkyl, mercaptomethyl, 1-H-imidazol-4-ylmethyl, methylthioethyl, pyrrolidinyl, hydroxymethyl, hydroxyethyl, or methylbenzyl unsubstituted or substituted with 1-3 hydroxyl, methoxy or ethoxy.

2. The compound of claim 1 wherein R$_1$ is methyl.

3. The compound of claim 1 wherein Z$_2$ is H, Z$_1$ is C=C—CO—NR$_2$R$_3$ optionally substituted with C$_1$-C$_3$ alkyl on the vinyl group, and R$_2$ and R$_3$ are as defined in claim 1.

4. The compound of claim 1 wherein R$_2$ is H, R$_3$ is

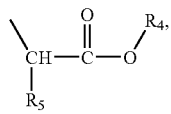

R$_4$ is methyl, and R$_5$ is isopropyl or methylbenzyl substituted with 0-3 hydroxyl, methoxy or ethoxy.

5. The compound of claim 4 wherein R$_5$ is methylbenzyl substituted with 2 methoxy.

6. The compound of claim 4 wherein R$_5$ is unsubstituted methylbenzyl.

7. The compound of claim 4 wherein R$_5$ is isopropyl.

8. The compound of claim 1 wherein R$_2$ and R$_3$ together form an optionally substituted 8-12 membered bicyclic ring.

9. The compound of claim 1 being selected from one of the following Compounds A-F:

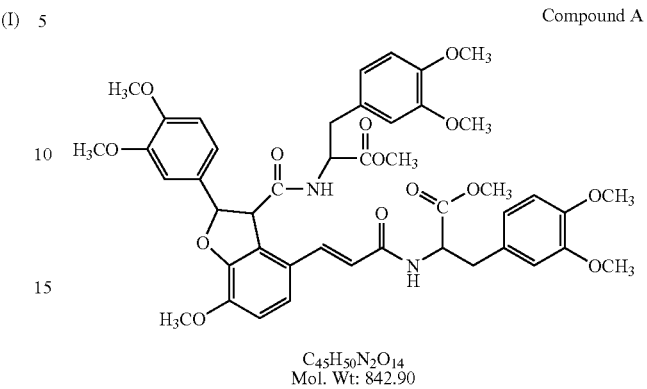

Compound A

C$_{45}$H$_{50}$N$_2$O$_{14}$
Mol. Wt: 842.90

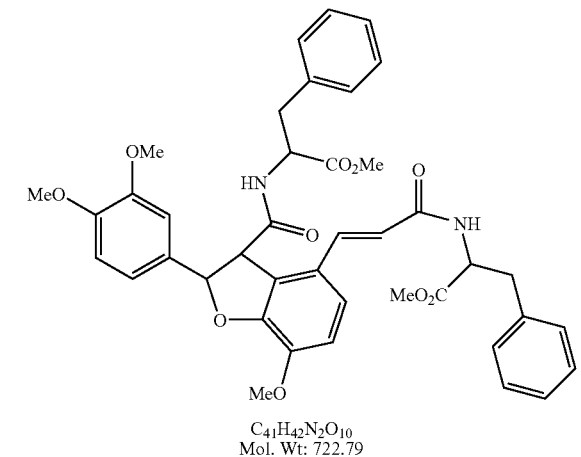

Compound B

C$_{41}$H$_{42}$N$_2$O$_{10}$
Mol. Wt: 722.79

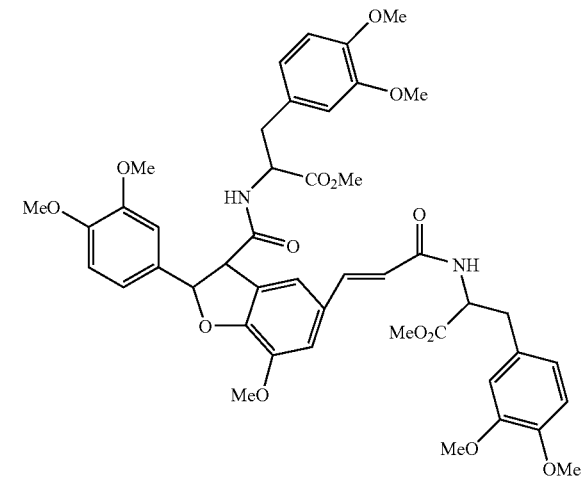

Compound C

C$_{45}$H$_{50}$N$_2$O$_{14}$
Mol. Wt: 842.90

-continued

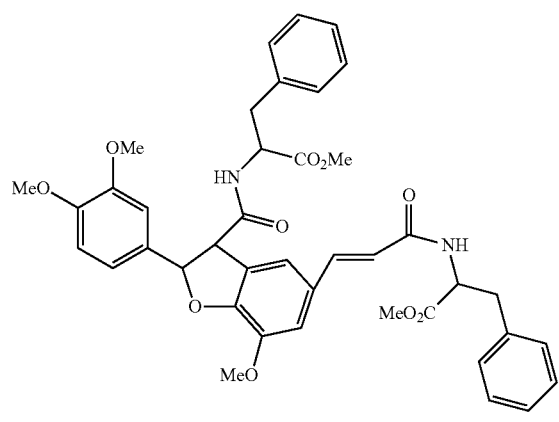

Compound D

C₄₁H₄₂N₂O₁₀
Mol. Wt: 722.79

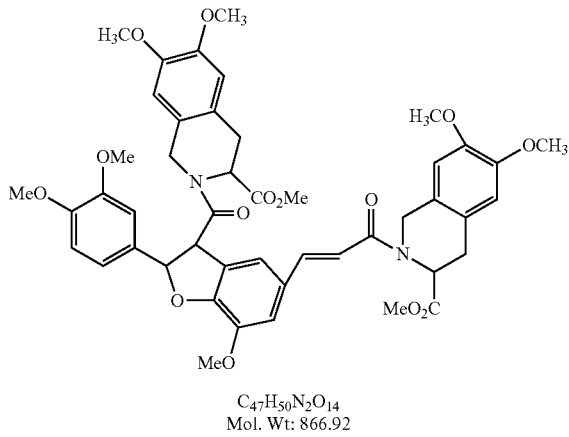

Compound E

C₄₇H₅₀N₂O₁₄
Mol. Wt: 866.92

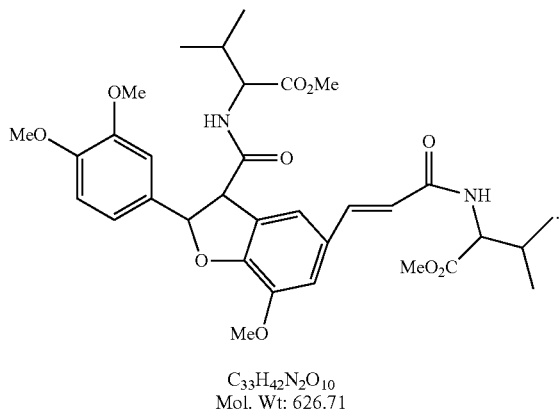

Compound F

C₃₃H₄₂N₂O₁₀
Mol. Wt: 626.71

10. The compound of claim 9 wherein the compound is one of Compounds A-C.

11. The compound of claim 9 wherein the compound is Compound A.

12. A method of treating a disease selected from hypertension, tumor, atherosclerosis, and myocardial infarction comprising administering to a patient in need thereof the compound of claim 1 or salt thereof in an effective amount.

13. A pharmaceutical composition comprising an effective amount of the compound of claim 1 or salt thereof, and a pharmaceutically acceptable carrier.

14. The pharmaceutical composition of claim 13 wherein the compound is one of Compounds A-C

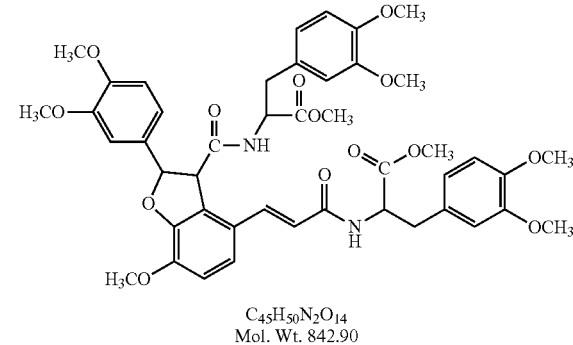

Compound A

C₄₅H₅₀N₂O₁₄
Mol. Wt: 842.90

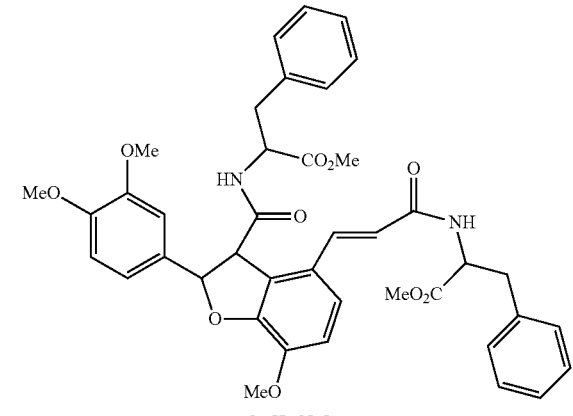

Compound B

C₄₁H₄₂N₂O₁₀
Mol. Wt: 722.79

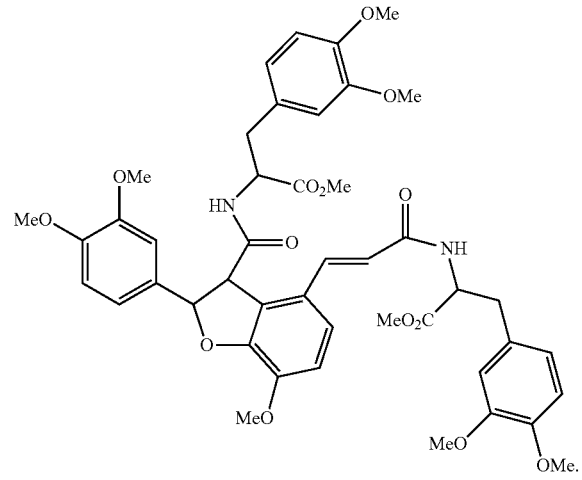

Compound C

C₄₅H₅₀N₂O₁₄
Mol. Wt: 842.90

15. The pharmaceutical composition of claim 14 wherein the compound is Compound A.

* * * * *